United States Patent
Hood et al.

(10) Patent No.: US 6,872,787 B2
(45) Date of Patent: *Mar. 29, 2005

(54) POST-TREATMENT OF A POLYMERIC COMPOSITION

(75) Inventors: David K. Hood, Basking Ridge, NJ (US); Michael Tallon, Aberdeen, NJ (US); John Mc Kittrick, Jersey City, NJ (US)

(73) Assignee: ISP Investments Inc., Wilmington, DE (US)

( * ) Notice: Subject to any disclaimer, the term of this patent is extended or adjusted under 35 U.S.C. 154(b) by 140 days.

This patent is subject to a terminal disclaimer.

(21) Appl. No.: 10/388,697

(22) Filed: Mar. 14, 2003

(65) Prior Publication Data

US 2003/0181578 A1 Sep. 25, 2003

Related U.S. Application Data

(63) Continuation-in-part of application No. 09/881,906, filed on Jun. 15, 2001, now Pat. No. 6,713,538, which is a continuation-in-part of application No. 09/784,268, filed on Feb. 15, 2001, now Pat. No. 6,548,597, which is a continuation-in-part of application No. 09/663,010, filed on Sep. 15, 2000, now Pat. No. 6,620,521.

(51) Int. Cl.$^7$ .............................................. C08C 19/00
(52) U.S. Cl. ........................ 525/385; 524/23; 524/808; 525/326.9; 525/342; 525/374; 525/375; 525/384
(58) Field of Search ................ 524/23, 808; 525/326.9, 525/342, 374, 375, 384, 385

(56) References Cited

U.S. PATENT DOCUMENTS

| | | | | | |
|---|---|---|---|---|---|
| 5,731,365 | A | * | 3/1998 | Engelhardt et al. | 523/206 |
| 6,133,369 | A | * | 10/2000 | Houben et al. | 524/555 |
| 6,187,872 | B1 | * | 2/2001 | Yanase et al. | 525/330.2 |
| 6,297,335 | B1 | * | 10/2001 | Funk et al. | 526/317.1 |
| 6,565,768 | B1 | * | 5/2003 | Dentler et al. | 252/194 |
| 6,713,538 | B2 | * | 3/2004 | Hood et al. | 524/23 |

* cited by examiner

*Primary Examiner*—Helen L. Pezzuto
(74) *Attorney, Agent, or Firm*—William J. Davis; Walter Katz

(57) ABSTRACT

A post-treatment process for making a water-resistant polymeric composition which is inkjet printable, or in the form of a strongly-swellable gel, includes providing a stable, aqueous two-phase polymeric composition by the steps of forming a reaction mixture in a reaction vessel which includes a water-soluble vinyl monomer, optionally with one or more water-soluble comonomers, a first amount of a multi-vinyl crosslinking agent, and water, heating the mixture, then periodically adding a predetermined amount of a free radical initiator, and polymerizing the reaction mixture, optionally removing the resultant two-phase polymeric composition from the reaction vessel, adding a predetermined amount of a post-treatment crosslinker, optionally blending with a proteinaceous or other water compatible polymer material thereto, optionally coating the mixture onto a support, and optionally heating at room temperature or above, to increase the viscosity of the composition in a predetermined manner.

14 Claims, 1 Drawing Sheet

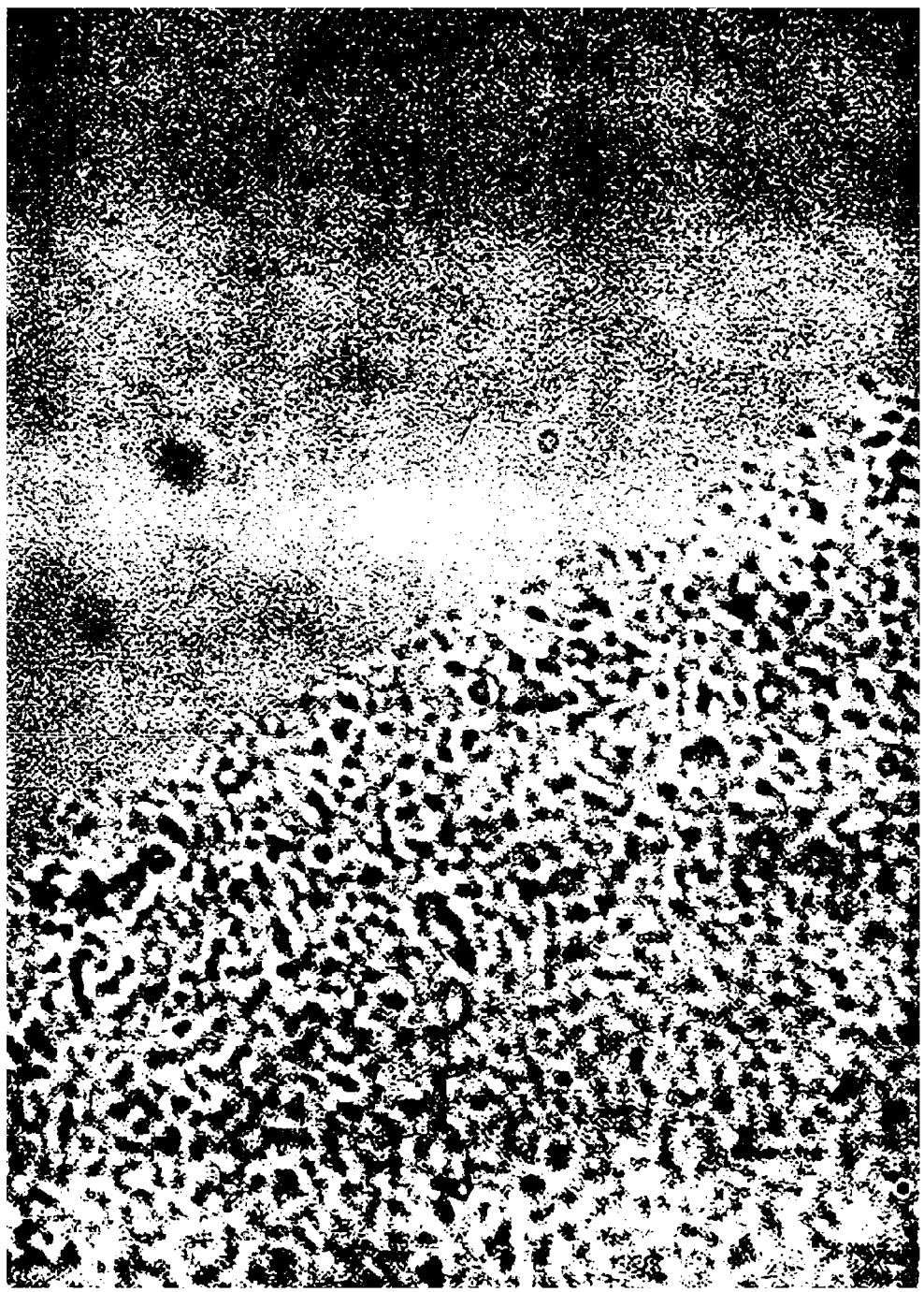

POST-TREATMENT OF A POLYMERIC COMPOSITION

CROSS-REFERENCE TO RELATED U.S. PATENT APPLICATIONS

This application is a continuation-in-part of co-pending U.S. patent application Ser. No. 09/663,010, filed Sep. 15, 2000, now U.S. Pat. No. 6,620,521 Ser. No. 09/784,268, filed Feb. 15, 2001, now U.S. Pat. No. 6,548,597 and Ser. No. 09/881,906, filed Jun. 15, 2001, now U.S. Pat. No. 6,713,538.

BACKGROUND OF THE INVENTION

1. Field of the Invention

This invention relates to water-resistant polymeric coatings or films, and highly-swellable polymeric gels, and, more particularly, to such products prepared from non-continuous, polymeric compositions having two phases therein, by further post-treatment crosslinking, and optionally blending of a proteinaceous compound or other water compatible polymer therewith during the post-treatment step.

2. Description of the Prior Art

Polymeric compositions of vinyl lactam monomers generally are one-phase, soluble, high viscosity materials. These compositions are found in a variety of commercial applications such as film formers, dye transfer inhibitors, rheology modifiers, extrusion components, dispersants, delivery systems, excipients, and drug delivery. Aqueous gels of these monomers can also be prepared by light covalent or associative crosslinking of polymer chains resulting in a highly-swellable, one-phase material of high viscosity. Such compositions are effective thickeners for use in personal care formulations such as hair care products.

The prior art is represented by the following:

Niessner, in U.S. Pat. Nos. 5,149,750 and 5,180,804, disclosed finely divided, water-swellable gel-like, water-swellable copolymers by polymerization of comonomers in the presence of a surfactant.

Liu, in U.S. Pat. No. 5,997,855, described a homogeneous terpolymer for hair care use, however, without a crosslinking agent.

Kopolow, in U.S. Pat. No. 5,130,121, described personal care compositions containing a stabilized cosmetically-active product obtained by in situ polymerization of a water-soluble vinyl monomer in the presence of discrete microdroplets of a cosmetically-active oil in water.

Blankenburg, in U.S. Pat. Nos. 5,635,169 and 6,107,397, described uncrosslinked aqueous copolymer dispersions of nonionic water-soluble monomers with N-vinyl groups, and hydrophobic monomers.

Steckler, in U.S. Pat. No. 3,878,175, disclosed highly absorbent spongy gel polymer materials by simultaneously copolymerizing and partially crosslinking a comonomer mixture of an alkyl acrylate and a heterocyclic N-vinyl monomer containing a carbonyl functionality in the presence of a hydrophobic liquid diluent in which the final polymer is insoluble.

Markus, in U.S. Pat. No. 2,810,716, described a process for making swellable resins by copolymerizing suitable monomers in the presence of a water-soluble non-redox divalent-ion containing salt.

Tseng, in U.S. Pat. Nos. 5,393,854 and 5,717,045, disclosed a one-phase, aqueous gel of crosslinked copolymers of vinyl pyrrolidone and dimethylaminoethyl methacrylate for use in hair care products. The crosslinking agent was 1-vinyl-3-(E)-ethylidene pyrrolidone. The gels had a Brookfield viscosity of between 60,000 and 100,000.

These references illustrate the desire of the art to produce a continuous network of polymer molecules, or microgel which is a one-phase system, and of high viscosity.

As described in the aforementioned co-pending U.S. patent applications, in contrast to this art, a new and improved aqueous polymeric composition was obtained which is a non-continuous polymeric composition having two-phases therein, particularly made up of a water-soluble polymer and in situ-formed, substantially water-insoluble resinous particles of the polymer substantially uniformly dispersed therein, and water or alcoholic solution. This polymeric composition is made by polymerizing a water-soluble vinyl monomer, such as a vinyl lactam, with a predetermined amount of a crosslinking agent, and water, at a selected temperature, e.g. 30–130° C., while periodically adding an initiator to the reaction mixture.

A particular application for such polymeric compositions is in color ink-jet printing. The advent of color inkjet printing has been instrumental in fueling the print-on-demand revolution and has also created a number of challenges. Often, the surface of the desired media does not possess the necessary properties for accepting the ink-jet ink. This results in long dry times and/or a poor ink-jet image. It has long been recognized that a surface treatment or media coating plays a critical role in the final print quality. Numerous media coatings are known in the art. They may contain any number of components and often consist of more than one layer. These ink-receptive coatings generally contain at least one hydrophilic polymer; often poly (vinylpyrrolidone) (PVP). In contrast to the teaching of the thickener art for personal care products, networked, highly swellable polymeric systems are undesirable in this application. Soluble PVP brings many benefits to properly formulated media coatings including rapid ink dry time, excellent print quality, highly resolved circular dots, and high, uniform optical density. Furthermore, copolymers of vinylpyrrolidone (VP) along with other suitable comonomers, such as dimethylaminoethyl methacrylate, acrylic acid, or vinyl acetate, have been used separately or in conjunction with PVP, to further optimize performance. Unfortunately, their resistance to water penetration can be weak. It is desired to provide long-term, excellent water-resistant qualities for such films.

Accordingly, it is an object of the present invention to provide a post-treatment composition and process for a two-phase, aqueous polymeric composition which can provide advantageous water-resistant polymeric coatings or films, inkjet printable polymeric compositions, and/or a highly-swellable polymeric gel.

Another object of the invention is to provide post-polymerization of such two-phase composition by further polymerization via crosslinking with a post-treatment crosslinker, to provide the desired water-resistant color inkjet-receptive film coated with the defined post-treated polymer composition of the invention, which film is capable of being printed from a color ink-jet printer to form superior water-resistant color images thereon.

Still another object of the invention is to provide a post-treatment of such two-phase composition by further blending with a post-treatment crosslinker and optionally a proteinaceous or other water compatible polymeric material, to provide the desired water-resistant color inkjet-receptive film coated with the defined post-treated inkjet printable polymer composition of the invention, which film is capable of being printed from a color ink-jet printer to form superior water-resistant color images thereon.

Another object of the invention is to provide a post-treatment method of making a two-phase polymeric hydrogel composition.

These and other objects and features of the invention will be made apparent from the following description of the invention.

IN THE DRAWING

The FIGURE is a photomicrograph of the aqueous polymeric composition of the invention showing the presence of two discrete phases therein.

SUMMARY OF THE INVENTION

What is described herein is a post-treatment product and process for making a water-resistant polymeric coating and a strongly-swellable polymeric gel which comprises (1) providing a stable, aqueous two-phase polymeric composition by the steps of (a) a reaction mixture in a reaction vessel of a water-soluble vinyl monomer, optionally with one or more water-soluble comonomers, a predetermined amount of a first crosslinking agent, and water, heating the mixture, then periodically adding a predetermined amount of an initiator, and polymerizing at a suitable temperature, e.g. at about 30–130° C., optionally removing said resultant two-phase composition from the reaction vessel, adding a predetermined amount of a post-treatment crosslinker, and optionally adding a proteinaceous and/or other water compatible polymer material thereto, optionally casting the mixture onto a support, and optionally heating to further crosslink the mixture.

DETAILED DESCRIPTION OF THE INVENTION

As described in the aforementioned co-pending applications, the polymeric composition of the invention includes a substantially water-insoluble polymer which is a crosslinked or branched polymer, which may be neutralized and/or quaternized, and/or functionally quaternized. Suitably the ratio of (a):(b) is 20–95% to 5–80%, preferably 20–75% to 25–80%. The crosslinking agent suitably is a substantially water-insoluble compound, for example, a multi-vinyl compound such as pentaerythritol triallyl ether (PETE), or pentaerythritol tetraacrylate (PETA); however, which is preferably at least partially soluble in water, and suitably present in an amount of 0.02–0.5% by weight of monomers in the composition, preferably 0.05–0.3%.

The aqueous two-phase polymeric composition is made by the steps of: providing a reaction mixture of a water-soluble vinyl monomer, optionally with one or more water-soluble comonomers, and a predetermined amount of the crosslinking agent, and water, heating the mixture, then periodically adding a predetermined amount of an initiator, such as an azo initiator, and polymerizing the reaction mixture, preferably at about 30–130° C., optionally, including the step of diluting with water during or after the polymerization.

Suitably, the polymer is a vinyl lactam polymer, optionally copolymerized with a comonomer such as methacrylate/acrylate and/or methacrylamide/acrylamide comonomer, or hydroxy ethyl methacrylate.

Most preferably, the vinyl lactam polymer is polyvinylpyrrolidone (PVP), poly(vinylcaprolactam) (PVCL), a copolymer of PVP and/or PVCL, and, optionally, one or more comonomers, including comonomers such as dimethylaminopropyl(meth)acrylamide (DMAPMA), dimethylaminoethyl(meth)acrylate (DMAEMA) and hydroxyethyl methacrylate (HEMA).

In this invention, the resinous particles of the composition have a size of <500μ, preferably <100μ, and optimally between >1 nm and <500μ.

The pre-post-treated composition usually has a Brookfield viscosity of 1,000 to 45,000 cps, preferably 2,000 to 20,000.

The two-phase compositions then may be dried, if desired, to provide the polymeric composition as a solid, and, further, the water-soluble polymer may be extracted with a solvent. The dried stable polymeric composition thereby includes, by weight, (a) 20% to 95% of a water-soluble polymer, and (b) 5% to 80% of in situ-formed, substantially water-insoluble resinous particles of said polymer substantially uniformly dispersed therein.

The post-treatment step of the invention includes, optionally, removing the two-phase polymeric composition from the reaction vessel, optionally drying, then adding a non-vinyl crosslinking agent, optionally a proteinaceous and/or other water compatible polymeric material, and further crosslinking or blending to form the desired water-resistant inkjet printable composition or hydrogel. The reaction mixture may be applied to a substrate, such as a polyester film, before post-treatment. A highly-swellable polymeric gel is made by limiting the amount of such crosslinker added. A highly viscous polymeric hydrogel is made by allowing the additional crosslinker to be present for a considerable period of time.

Suitable additional crosslinking agents during the post-treatment step of forming the water-resistant inkjet printable compositions or hydrogel product include crosslinking agents suitable for forming the 2-phase composition, and other crosslinking agents available in the chemical industry, e.g. an aziridine, e.g. XAMA-7, trimethylolpropane tris(2-methyl-1-aziridine propionate), an epoxy-based compound, e.g. an oxirane or glycidyl compound, e.g. glycerol diglycidyl ether. Proteainaceous materials, such as skin gelatin, and/or other water compatibe materials, such as polyvinyl alcohol (PVOH), 2-ethyl-2-oxazolidone (PEOX), and polyethyleneoxide (PEO), also may be used.

Accordingly, a post-treatment crosslinking agent may be a polyfunctional aziridine such as the following compounds:

(1) trimethylolpropane-tris-(β-(N-aziridinyl)propionate)

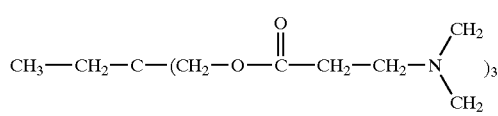

(2) pentaerythritol-tris-(β-(N-aziridinyl)propionate)

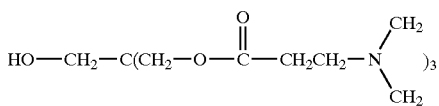

(3) trimethylolpropane-tris-(β-(N-methylaziridinyl propionate)

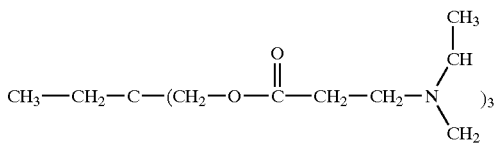

and the like, which have at least two crosslinking sites in each molecule.

The chemical name of aziridine is: 1-aziridinepropanoic acid, or 2-methyl-2-ethyl-2-[3-(2-methyl-1-aziridinyl)-1-oxopropoxylmethyl]1, 3-propandiyl ester; (Zeneca Resins, Wilmington, Mass., sold as CX-100). XAMA-7, Bayer Corp.

Accordingly, a post-treatment crosslinking agent may be a polyfunctional epoxy or oxirane such as the following compounds: Glycerol diglycidal ether, and the like, 3-glycidoxyprooyltrimethoxysilane (Dow Corning Product Z-6040 and Witco's Silquest A-187 Silane) Beta-(3,4-epoxycyclohexyl)ethyltriethoxysilane (Witco's CoatOSil 1770 Silane) Exo-3,6-epoxy-1,2,3,6-tetrahydrophthalic anhydride.

The degree of additional crosslinking achieved during the post-treatment step will depend upon, for example, the particular post-treatment crosslinker used, its reaction kinetics with the polymer(s), the time of contact of crosslinker in the solution, effect of any stabilizers or other additives, the amount of crosslinker used, and the temperature of reaction. Accordingly, high solids, inkjet printable compositions of desired viscosity which form water-resistance coatings can be made by this step as well as highly viscous polymeric hydrogels.

The invention will now be illustrated in more detail by reference to the following examples.

Preparation of Two-Phase, Aqueous Polymeric Compositions

EXAMPLE 1

VP/DMAPMA/Neutralized

1. To a 2-l kettle fitted with a nitrogen inlet tube, thermocouple, agitator, and feed lines was added 87.15 g of vinyl pyrrolidone monomer, (VP), 697 g DI water and 0.275 g (0.25% based upon monomer) of pentaerythritol triallyl ether (PETE) as crosslinker.
2. Purged with nitrogen subsurface for 30 minutes.
3. Heated to 70° C.
4. In a separate container weighed out 22.69 g of dimethylaminopropyl methacrylamide (DMAPMA).
5. With kettle temperature at 70° C., stop subsurface nitrogen purge and purged above surface. Precharged 1.1 g DMAPMA from container.
6. Started continuous addition of the remaining DMAPMA (21.86 g) over 210 minutes at a flow rate 0.11 ml/minute. Once the DMAPMA flow started, initiated with first shot of Vazo® 67 in isopropanol (IPA) (Time 0).
7. Initiator was added in 5 separate shots at 0, 30, 60, 150 and 210 minutes. 0.2 g of Vazo® 67 in 1.0 g IPA was added for each shot and two 0.5 g IPA washes were made.
8. Held the reaction temperature overnight at 70° C.
9. When residual VP level was below 400 ppm, diluted the batch with 266.7 g of DI water.
10. Cooled batch to 50° C.
11. Neutralized the batch with conc. HCl to pH of 6.2–6.8 at 50° C. Room temperature pH was 6.8–7.2. Required approximately 14 g of conc. HCl.
12. Added 0.15 to 0.19% BTC 50 NF as preservative.
13. A two-phase, aqueous polymeric composition was obtained as shown in the FIGURE.

EXAMPLE 2

The process of Example 1 was repeated using 5 separate shots of 0.3 g each of Vazo® 67 in 1.0 g of IPA. A polymeric composition similar to Example 1 was obtained.

EXAMPLE 3

The process of Example 1 was repeated using 5 separate shots of 0.4 g each of Vazo® 67 in 1 g of IPA, and 0.3 g of crosslinker. A similar polymeric composition was obtained.

EXAMPLE 4

PVP

1. To a 2-l kettle fitted with a nitrogen inlet tube, thermocouple, agitator, and feed lines was added 131.81 g of VP, 756 g DI water and 0.197 g PETE (0.15% based upon monomer).
2. Purged with nitrogen subsurface for 30 minutes.
3. Heated to 70° C.
4. Initiator was added at 0 and 30 minutes. 0.48 g of Vazo® 67 in 1.5 g IPA was added for each shot and two 1.0 g IPA washes were made.
5. Held the reaction temperature overnight at 70° C.
6. When residual VP was below 400 ppm, diluted the batch with 320.04 g DI water.
7. Cooled batch to 50° C.
8. Added 0.15 to 0.19% BTC 50 NF as preservative.
9. The product was a 2-phase, polymerization composition with 40 to 70% resinous particles, whose soluble fraction had a weight average molecular weight of 1,200,000 to 1,500,000.
10. A two-phase, aqueous polymeric composition as shown in the FIGURE was obtained.

EXAMPLE 5

VP/DMAPMA/Quaternized with Diethyl Sulfate

1. To a 2-l, kettle fitted with a nitrogen inlet tube, thermocouple, agitator, and feed lines was added 96.00 g of VP, 702.7 g DI water and 0.36 g PETE (0.30% based upon monomer).
2. Purged with nitrogen subsurface for 30 minutes.
3. Heated to 70° C.
4. In a separate container weighed out 24.0 g DMAPMA and 74.7 g DI water. Purged with nitrogen.
5. When kettle temperature was at 70° C., stopped subsurface nitrogen purge and purged above surface. Precharged 4.94 g DMAPMA/water from container.
6. Started continuous addition of the remaining DMAPMA/water (93.76 g) over 210 minutes. Flow rate 0.48 ml/minute. Once DMAPMA/water flow started, initiated with first shot of Vazo® 67 in IPA (Time 0).
7. Initiator was added at 0, 30, 60, 150 and 210 minutes. 0.44 g of Vazo 67 in 1.3 g IPA was added for each shot and two 0.7 g IPA washes were made.
8. Held the reaction temperature overnight at 70° C.
9. When residual VP was below 400 ppm, diluted the batch with 297.5 g DI water.

10. Cooled batch to 50° C.
11. Neutralized the batch with 19.56 g diethyl sulfate (DES) over 60 minutes; at flow rate of 0.28 g/ml.
12. Stirred for 2 hours.
13. Product.
14. A two-phase, aqueous polymeric composition as shown in the FIGURE was obtained.

EXAMPLE 6

VP/DMAPMA Neutralized with Benzophenone-4

1. To a 2-l kettle fitted with a nitrogen inlet tube, thermocouple, agitator, and feed lines was added 87.15 g of HPVP, 630 g DI water and 0.33 g PETE (0.30% based upon monomer).
2. Purged with nitrogen subsurface for 30 minutes.
3. Heated to 70° C.
4. Weighed out 22.69 g DMAPMA and 67 g DI water. Purged with nitrogen.
5. When kettle temperature was at 70° C., stopped subsurface nitrogen purge and purged above surface. Precharged 4.23 g DMAPMA/water from container.
6. Started a continuous addition of the remaining DMAPMA/water (85.46 g) over 210 minutes. Flow rate 0.40 ml/minute. Once DMAPMA/water flow started, initiated with first shot of Vazo® 67 in IPA (Time 0).
7. Initiator was added at 0, 30, 60, 150 and 210 minutes. 0.4 g of Vazo 67 in 1.0 g IPA was added for each shot and two 0.5 g IPA washes were made.
8. Held the reaction temperature overnight at 70° C.
9. When residual VP was below 400 ppm, diluted the batch with 266.7 g DI water.
10. Cooled batch to 50° C.
11. Neutralized the batch with benzophenone-4, 5 to 99 mole % (2 to 38.6 g respectively). Continued neutralization with sulfuric acid to pH of 6.8 to 7.8 at 50° C.
12. Cooled and discharged.
13. Product.
14. A two-phase, aqueous polymeric composition as shown in the FIGURE was obtained.

EXAMPLE 7

VP/DMAPMA

1. To a 2-l kettle fitted with a nitrogen inlet tube, thermocouple, agitator, and feed lines was added 104.58 g of HPVP, 756 g DI water and 0.59 g pentaerythritol tetra acrylate (0.30% based upon monomer).
2. Purged with nitrogen subsurface for 30 minutes.
3. Heated to 70° C.
4. In a separate container, weighed out 27.23 g DMAPMA and 80.4 g DI water. Purged with nitrogen.
5. When kettle temperature was at 70° C., stopped subsurface nitrogen purge and purged above surface. Precharged 5.38 g DMAPMA/water from container.
6. Started continuous addition of the remaining DMAPMA/water (102.25 g) over 210 minutes. Flow rate 0.52 ml/minute. Once DMAPMA/water flow started, initiated with first shot of Vazo®67 in IPA (Time 0).
7. Initiator was added at 0, 30, 60, 150 and 210 minutes. 0.16 g of Vazo® 67 in 1.0 g IPA was added for each shot and two 0.5 g IPA washes were made.
8. Held the reaction temperature overnight at 70° C.
9. When VP was below 400 ppm, diluted the batch with 266.7 g DI water.
10. Cooled batch to 50° C.
11. Neutralized the batch with conc. sulfuric acid to pH of 6.6 to 7.8 at 25° C.
12. Added 0.15 to 0.19% BTC 50 NF as preservative.
13. Product.
14. A two-phase, aqueous polymeric composition as shown in the FIGURE was obtained.

EXAMPLE 8

Vinyl Caprolactam/DMAPMA

1. To a 2-l kettle fitted with a nitrogen inlet tube, thermocouple, agitator and feed lines was added 130.7 g vinyl caprolactam, 128.7 g DI water, 171.6 g ethanol, and 0.88 g PETE (0.6% based upon monomer).
2. Purged with nitrogen for 30 minutes.
3. Heated to 70° C.
4. In a syringe pump was added 32.98 g DMAPMA and 171.6 g DI water.
5. At 70° C. added 40 ml of the DMAPMA/water mixture to the kettle and added the first shot of initiator, 0.075 g Vazo® 67 in 0.75 g ethanol. Washed with 0.75 g ethanol.
6. Started addition of the remaining DMAPMA/water mixture (Time 0) from the syringe pump at a rate of 0.34 ml/min, added over 480 minutes.
7. At time 60, 120, 180, 240, 300, 360, 420 and 480 minutes added a shot of Vazo® 67, 0.075 g in 0.75 g ethanol. Washed with 0.75 g ethanol.
8. Held at 70° C. overnight.
9. Cooled reaction to 30° C. and added 415.6 g DI water.
10. Mixed until uniform and then added 544.4 g DI water and 15.38 g hydrochloric acid.
11. Mixed for 2 hours. Adjusted pH to 6.6 to 7.8 with hydrochloric acid, if necessary.
12. Added 0.15 to 0.19% BTC-50 NF as preservative.
13. Product.
14. A two-phase, aqueous polymeric composition as shown in the FIGURE was obtained.

EXAMPLE 9

VP/DMAEMA

1. To a 2-l kettle fitted with a nitrogen inlet tube, thermocouple, agitator, and feed lines is added 87.15 g of HPVP, 630 g DI water and 0.33 g (0.30% based upon monomer) pentaerythritol triallyl ether.
2. Purged with nitrogen subsurface for 30 minutes.
3. Heated to 70° C.
4. In a separate container, weighed out 22.69 g DMAEMA and 67 g DI water. Purged with nitrogen.
5. When kettle temperature was at 70° C., stopped subsurface nitrogen purge and purged above surface. Precharged 4.23 g DMAEMA/water from container.
6. Started continuous addition of the remaining DMAEMA/water (85.46 g) over 210 minutes. Flow rate 0.40 ml/minute. Once DMAEMA/water flow started initiator addition with first shot of Vazo 67 in IPA (Time 0).
7. Initiator was added at 0, 30, 60, 150, and 210 minutes. 0.4 g of Vazo 67 in 1.0 g IPA was added for each shot and two 0.5 g IPA washes were made.
8. Held the reaction temperature overnight at 70° C.
9. When VP was below 400 ppm, diluted the batch with 266.7 g DI water.
10. Cooled batch to 50° C.
11. Neutralized the batch with conc. HCl to pH of 6.2 to 6.8 at 50° C. Room temperature pH will be 6.8 to 7.2. Required approximately 14 g of conc. HCl.

12. Added 0.15 to 0.19% BTC 50 NF as preservative.
13. A two-phase, aqueous polymeric composition as shown in the FIGURE was obtained.

EXAMPLE 10

Drying of Example 9

The solution of Example 9 was dried on a drum dryer to a solids content of >95%. The Tg of the powder was 167° C. Then it was reconstituted in water and found to provide the same waterproofing as the original solution.

EXAMPLE 11

Particle Isolation and Properties 95.2 g of approximately 10% solids content of the two-phase polyvinylpyrrolidone composition of Example 1 was diluted in 2-liters of distilled water and stirred until thoroughly mixed. A second solution was prepared by taking 500 ml of the first solution and diluting in 2-liters of distilled water. Stirred until thoroughly mixed. Poured the second solution into four 16 oz. jars and centrifuged at ~2250 rpm for about 90 minutes. A white precipitate was observed on the bottom of each 16 oz. jar. The precipitate was removed via pipette and placed into four 8-dram vials, respectively. The four 8-dram vials were centrifuged at ~3000 rpm for 60 minutes. The particle size of the precipitate was measured using a Microtrak UPA and found to be about 4 nanometers.

EXAMPLE 11A

The precipitate obtained in Example 11 in three 8-dram vials was dried, in vacuo in a 40° C. oven overnight. The result was a thin, generally clear film upon visual observation. This material was then exposed successively to methanol, diethyl ether and n-heptane. After 24 hours, methanol had re-dispersed the material. Diethyl ether and n-heptane did not appear to effect the dried material. After 14 days, all samples exhibited a similar appearance to the original 24 hour observations. The particle size of the methanol dispersed material was measured using a Microtrak UPA and found to be about 4 microns.

COMPARATIVE EXAMPLE 12

An aqueous solution of 119.64 g of vinyl pyrrolidone monomer, 0.36 g pentaerythritol triallyl ether (PETE), 0.6 g of Vazo 67, and 480 g water was charged to a kettle and purged with nitrogen. The reaction mixture was then heated to 65° C. while stirring at 650 rpm. Within 25 minutes the product became so viscous that the reaction was stopped. The product was a continuous gel only.

COMPARATIVE EXAMPLE 13

An aqueous solution of 119.64 g of vinyl pyrrolidone monomer, 0.36 g pentaerythritol triallyl ether (PETE), 0.23 g of Vazo 67, and 480 g water was charged to a kettle and purged with nitrogen. The reaction mixture was then heated to 65° C. while stirring at 650 rpm. After 2 hours at 65° C., the reaction was heated to 95° C. for 1 hour. The product was a viscous solution only.

B. Post-Treatment of Polymeric Compositions

Post-Treatment of (VP/DMAPMA/Neutralized/HCl) with Aziridine as Post-Treatment Crosslinker

EXAMPLE 14

Polymeric compositions of VP/DMAPMA/PETE neutralized with HCl, as described in Examples 1–3, were removed from the reactor vessel, and additional crosslinker was added. The crosslinker was a polyfunctional aziridine compound, XAMA® 7, from Bayer, which was added at various weight percents of crosslinker, as given in the Table below. Draw-downs from a 10% aqueous solution of the mixture then were cast onto a polyester substrate using a #38 Mayer bar, allowed to dry and polymerize in an oven at 100° C. for 10 minutes. A dry coating having a thickness of ~9 micron was obtained. Other suitable substrates include paper, vinyl film, and other organic or inorganic materials.

The thus-coated films were then printed using a HP 832C printer at 600 DPI in "HP Premium Photo Paper" mode. Individual blocks of cyan(C), magenta(M), yellow(Y), and black(K), approximately 1"×1.75" in size, were printed side by side.

The water-resistance of the film was measured by the following standard test procedure. The printed sheet was placed at a 45° angle and 10 ml of water at a constant rate of 2 ml/min was dripped over the surface. The samples were then judged by following rating system:

| | |
|---|---|
| Poor | All ink removed in less than 1 minute. |
| Fair | Most or all ink removed between 1 and 5 minutes. |
| Moderate | Some (<50%) loss of ink after 5 minutes. |
| Good | Very slight (<10%) loss of ink with minimal running. |
| Very Good | 100% water resistance with no change in appearance after 1 hour. |

Results

The results of these tests, shown in Table 1, establish that the polymeric composition post-treated with a suitable amount of additional crosslinking agent exhibited an advantageous water-resistant property.

TABLE 1

| Post-Treatment Crosslinker Wt. (%) | Water Resistance (Time) of Film |
|---|---|
| 0.0 | 12 min 22 sec |
| 0.5 | 16 min 8 sec |
| 1.0 | >1 hr |
| 1.5 | >1 hr |

EXAMPLE 15

Post-Treatment with Active Present 100 g of VP/DMAPA/PETE-$H_2SO_4$, (10% solids) (Ex. 1) was mixed with 0.01 g of a red food dye and 2 g D-limonene (fragrance) to give a homogeneous dispersion. Addition of 0.5 g of XAMA-7 (aziridine) crosslinker post-crosslinked the mixture. A hydrogel was formed in 2 hours at room temperature without further mixing. The product was a homogeneous dispersion, red gel with an orange odor, similar to an air-freshener.

Similarly modified hydrogels can be formed with other commercial hydrogel systems such as contact lens membranes and hydrogel delivery systems with pharmaceuticals and/or excipients/disintegrants.

EXAMPLE 15A

Room Temperature Post-Treatment of (VCL/DMAPMA/HEMA*/PETE/HCL) as Gel Composition 332.2 g of VCL/DMAPMA/HEMA/PETE/HCL, (10.2% solids in water, viscosity=36.8 cPs (LVT, 30 RPM, #61))

was mixed with 4.41 g of glycerol diglycidyl ether. After 1.5 hours the sample viscosity was 227,000 cPs (RVT, 10 RPM, #96) (Table 2). After one day the sample became a highly rigid hydrogel.

*hydroxyethyl methacrylate

EXAMPLE 15B

Example 15A was repeated using VCL/DMAPMA/HEMA/HCL and one of the following glycidyl or polyglycidyl compounds: tris(2,3-epoxypropyl) isocyanurate, diglycidyl ether of 1,4 butanediol, trimethylolpropane triglycidyl ether, diglycidyl 1,2-cyclohexanecarboxylate, neopentyl glycol diglycidyl ether, and 3-glycidoxypropyltrimethoxysilane, β-(3,4-epoxycyclohexyl) ethyltriethoxysilane or glycerol propoxylate triglycidyl ether as post-crosslinker. Similar results are obtained.

EXAMPLE 15C

The aziridine based crosslinkers sold as Neocryl® CX-100 (Cytex) and trimethylolpropane tris(2-methyl-1-aziridinepropionate) were used in place of the diglycidyl ether. Similar results are obtained.

TABLE 2

| Ex. No. | Brookfield Viscosity | | Condition | Time of Contact (min) |
| --- | --- | --- | --- | --- |
| 7 | 624 | | LV,30,#63 | 0 |
| | | 566 | LV,30,#63 | 0 |
| 7 | 126000 | | RV,10,#7 | 15 |
| | | 95500 | RV,20,#7 | 15 |
| 1 | 796 | | LV,30,#63 | 0 |
| | | 710 | LV,60,#63 | 0 |
| 1 | 104000 | | LV,0.6,#63 | 15 |
| | | 63600 | LV,1.5,#63 | 15 |
| 7 | 488 | | LV,30,#63 | 0 |
| | | 450 | LV,60,#63 | 0 |
| 2 | 132000 | | LV,0.3,#63 | 15 |
| | | 82200 | LV,0.6,#63 | 15 |
| 15A | 36.8 | | LV,30,#61 | 0 |
| | | 37.2 | LV,60,#61 | 0 |
| 15A | 39.8 | | LV,30,#61 | 15 |
| | | 39.8 | LV,60,#61 | 15 |
| 15A | 227000 | | | 90 |

EXAMPLE 16

Post Treatment of (VP/DMAPMA/PETE/Sulfuric Acid) with Proteinaceous Material for Post-Treatment Step To improve water resistance to the transparent inkjet printed film, the two-phase, polymeric composition comprised of VP/DMAPMA/PETE neutralized with sulfuric acid (Ex. 1) was blended with the proteinaceous material, skin gelatin at 50/50 wt. %. This was accomplished by first mixing the gelatin into pre-heated 60° C. water (10 wt. %). Then the VP/DMAPMA/PETE composition was mixed into the gelatin/water mixture. Draw-downs of this composition were cast onto a polyester substrate using a #38 Mayer bar and allowed to dry in an oven at 90° C. for approximately 5 minutes to give a dry coating thickness of ~9 micron.

After standing for 3 hours at room temperature, the coated sample was inkjet printed using an Epson Stylus 800. Individual blocks of cyan(C), magenta(M), yellow(Y), and black(K), approximately 1"×1.75" in size, were printed side by side.

Water-resistance of the coating was measured by the following standard test procedure: placing the printed sheet at a 45° C. angle and dripping at least 10 ml of water at a constant rate (2 ml/min) over the surface. The samples were then judged by following rating system:

| | |
| --- | --- |
| Poor | All ink removed in less than 1 minute. |
| Fair | Most or all ink removed between 1 and 5 minutes. |
| Moderate | Some (<50%) loss of ink after 5 minutes. |
| Good | Very slight (<10%) loss of ink with minimal running. |
| Very Good | 100% water resistance with no change in appearance. |

Results

The results of these tests, shown in Table 3, establish that the two-phase polymeric composition, post treated with a proteinaceous material, exhibits an advantageous water-resistant property (dialdehyde). Note that for the VP/DMAPMA/PETE/Gelatin blend, no damage to imprinted surface was observed.

TABLE 3

| Sample | Gelatin (%) | Water Resistance Time |
| --- | --- | --- |
| VP/DMAPMA/PETE | 0.0 | ~12 min 20 sec |
| VP/DMAPMA/PETE | 50 | >30 min |

EXAMPLE 16A

The post-treatment process was carried out with glyoxal (polyaldehyde) as the post-treatment crosslinker. Similar results are obtained.

EXAMPLE 17

The post-treatment process is carried out with 3-glycidoxypropyl trimethoxysilane as the post-treatment crosslinker. Similar results are obtained.

EXAMPLE 18

Room Temperature Post-Treatment of (VP/DMAPMA/PETE/Sulfuric Acid) as Gel Composition 249.4 g of VP/DMAPMA/PETE/sulfuric acid, (6.0% solids in water, viscosity=1400 cPs (LVT, 30 rpm, #64)) was mixed with 1.04 g of glycidol and the mixture was kept at room temperature for 5 days. Then 0.35 g of boric acid was added and the sample was shaken vigorously. After 23 hours, a gel composition formed with a viscosity of 137,000 cPs (LVT, 0.6 rpm, #64).

EXAMPLE 18A

Room Temperature Post-Treatment of (VP/DMAPMA/PETE/HCL) as Gel Composition

The post-treatment process is carried out with 1-aziridineethanol followed by treatment with diglycidal ether of 1,4 butanediol. Similar results are obtained.

While the invention has been described with particular reference to certain embodiments thereof, it will be understood that changes and modifications may be made which are within the skill of the art. Accordingly, it is intended to be bound only by the following claims, in which:

What is claimed is:

1. A past-treatment process for making an inkjet printable, polymeric composition or a strongly-swellable polymeric hydrogel which comprises providing a stable, aqueous two-phase polymeric composition by the steps of forming a reaction mixture in a reaction vessel of a water-soluble vinyl monomer, optionally with one or more water-soluble comonomers, a predetermined amount of a first crosslinking agent, and water, heating the mixture, then periodically adding a predetermined amount of a free radical initiator, and polymerizing at a suitable temperature, optionally removing said resultant two-phase polymeric composition from the reaction vessel, including an added active material, adding a predetermined amount of a post-treatment crosslinker, optionally blending a proteinaceous and/or water compatible material thereto, optionally coating the mixture onto a support, and optionally heating the mixture.

2. A process according to claim 1 which produces an inkjet printable polymeric composition capable of forming a water-resistant polymeric coating on a substrate.

3. A process according to claim 1 which produces a hydrogel composition.

4. A process according to claim 1 in which said two-phase composition is post-treated with said post-treatment crosslinker at a temperature from room temperature to about 200° C.

5. A process according to claim 1 in which at least 0.02% by weight of said post-treatment crosslinker is added to the two-phase composition.

6. A process according to claim 1 which includes a proteinaceous material.

7. A process according to claim 1 in which said first polymerization crosslinker is present in an amount of 0.02–0.5 wt. % based on monomers.

8. A process according to claim 1 which produces a strongly-swellable hydrogel having a Brookfield viscosity of at least 100,000 cps.

9. A process according to claim 1 where the active material is present and is a cosmetic, nutritional or pharmaceutical active material.

10. A process according to claim 1 in which said water compatible material is polyvinyl alcohol, 2-ethyl-2-oxazolidone or polyethylene oxide.

11. A process according to claim 1 wherein said comonomer is dimethylaminopropyl(meth)acrylamide, dimethyl aminoethyl(meth) acrylate and/or hydroxyl ethyl(meth) acrylate.

12. A process according to claim 1 wherein the post-treatment crosslinker is an aziridine, 1-aziridine ethanol, glycidol, a glycerol glycidyl ether, tris(2,3-epoxypropyl) isocyanurate, trimethylolpropane triglycidyl ether, diglycidyl ether of 1,4 butanediol, diglycidyl 1,2-cyclohexanecarboxylate, neopentyl glycol diglycidyl ether, 3-glycidoxypropyltrimethoxysilane, β-(3,4-epoxycyclohexyl) ethyltriethoxysilane, glycerol propoxylate triglycidyl ether or glycidol, or boric acid.

13. A process according to claim 11 wherein said post-treatment crosslinker includes at least 2 crosslinking sites in the molecule.

14. A process claim 13 in which said post-treatment crosslinker is a polyfunctional epoxy or oxirane.

\* \* \* \* \*